United States Patent [19]

Papadofrangakis et al.

[11] 4,265,126
[45] May 5, 1981

[54] MEASUREMENT OF TRUE BLOOD VELOCITY BY AN ULTRASOUND SYSTEM

[75] Inventors: Emmanuel Papadofrangakis, Schenectady; William E. Engeler, Scotia, both of N.Y.; John A. Fakiris, Holly Hill, Fla.

[73] Assignee: General Electric Company, Schenectady, N.Y.

[21] Appl. No.: 48,711

[22] Filed: Jun. 15, 1979

[51] Int. Cl.³ .............................................. G01F 1/66
[52] U.S. Cl. .................................. 73/861.25; 128/663
[58] Field of Search ........................... 73/861.25, 602; 128/663

[56] References Cited

U.S. PATENT DOCUMENTS

| | | | |
|---|---|---|---|
| 3,766,517 | 10/1973 | Fahrbach | 73/861.25 |
| 3,939,707 | 2/1976 | Kossoff | 73/861.25 |
| 4,217,909 | 8/1980 | Papadofrangakis et al. | 128/663 |

FOREIGN PATENT DOCUMENTS 1398022 6/1975 United Kingdom ..................... 128/663

OTHER PUBLICATIONS

"Instantaneous Bi-dimensional Blood Velocity Profiles in the Major Vessels by a Pulsed Ultrasonic Doppler Velocimeter", Peronneau et al., Proceedings of the Second World Congress on Ultrasonics in Medicine, Rotterdam, 4-8 Jun. 1973, pp. 259-266, Excerpta Medica Amsterdam 1974, American Elsevier Publishing Company, Inc. New York.

Primary Examiner—Charles A. Ruehl
Attorney, Agent, or Firm—Donald R. Campbell; Marvin Snyder; James C. Davis

[57] ABSTRACT

Two components of the velocity of blood or similar liquids and the true flow vector are derived by a linear transducer array cross-beam configuration. Ultrasound pulses are transmitted from the center elements and backscattered echoes are received by left and right receiver sub-arrays whose locations depend on the observation point. A duplex imaging system with a sector scanner incorporates a Doppler modality with little added complexity and provides components of flow velocity parallel to and transverse to the acoustic beam direction from which the true velocity vector is computed.

17 Claims, 9 Drawing Figures

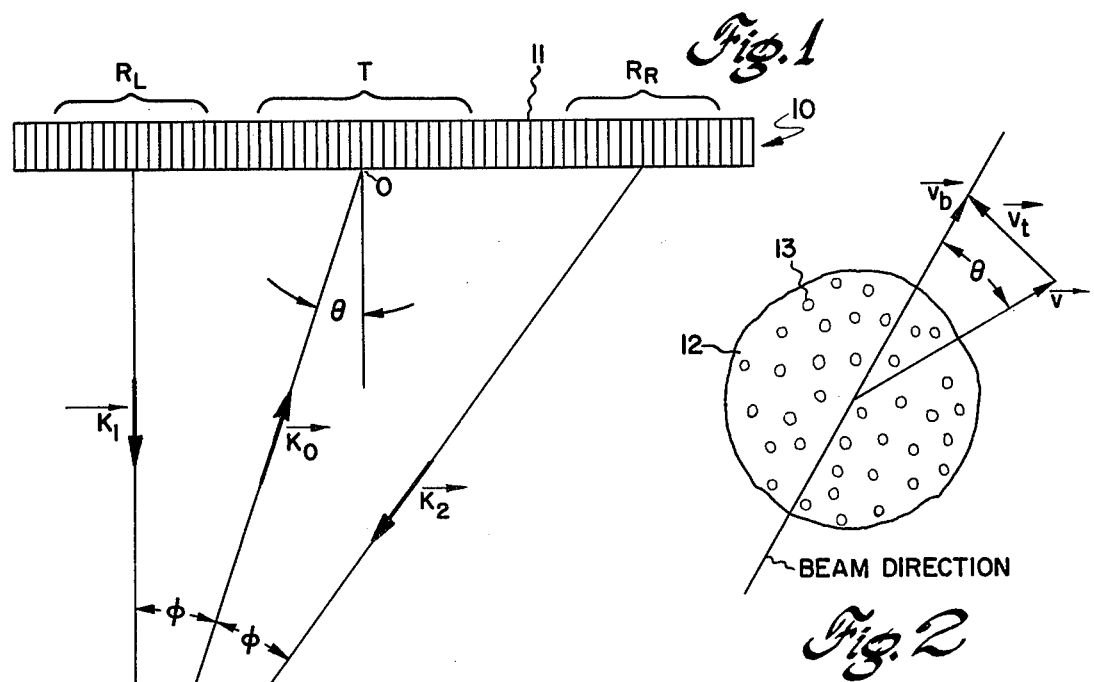
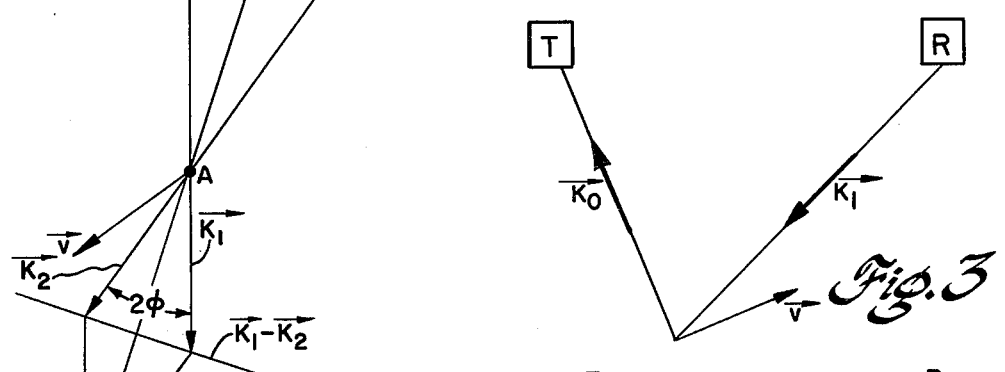
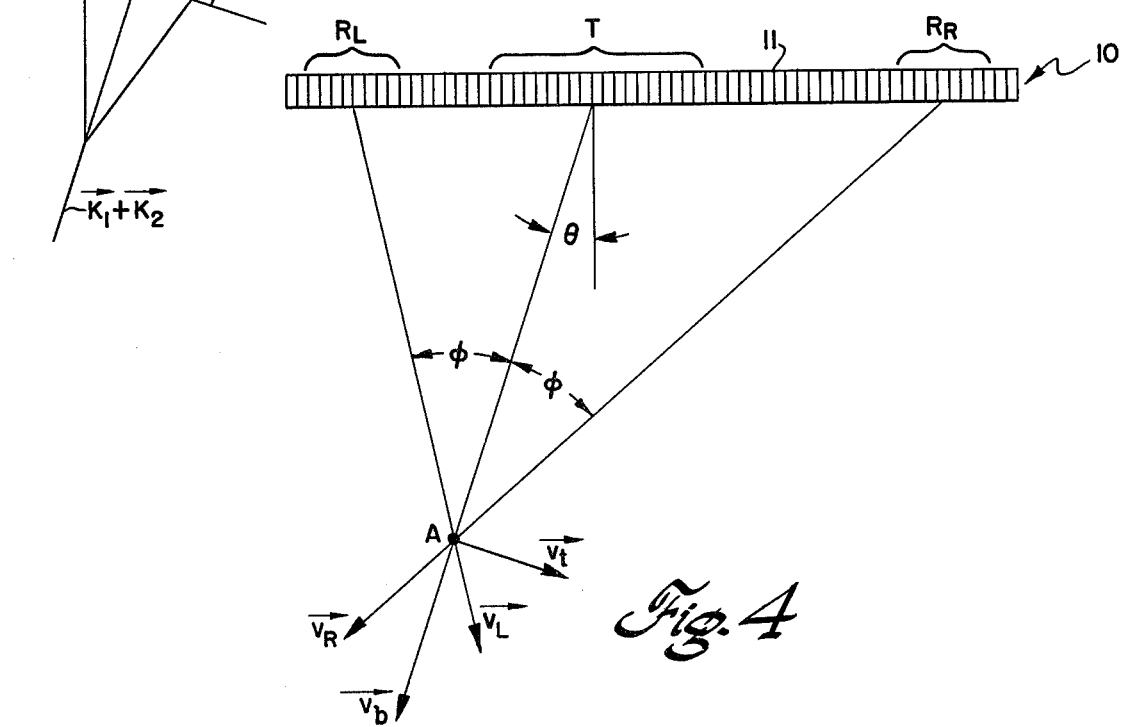
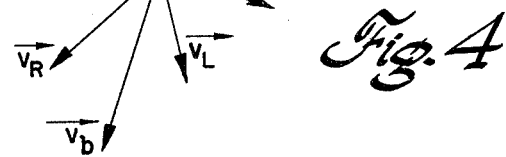

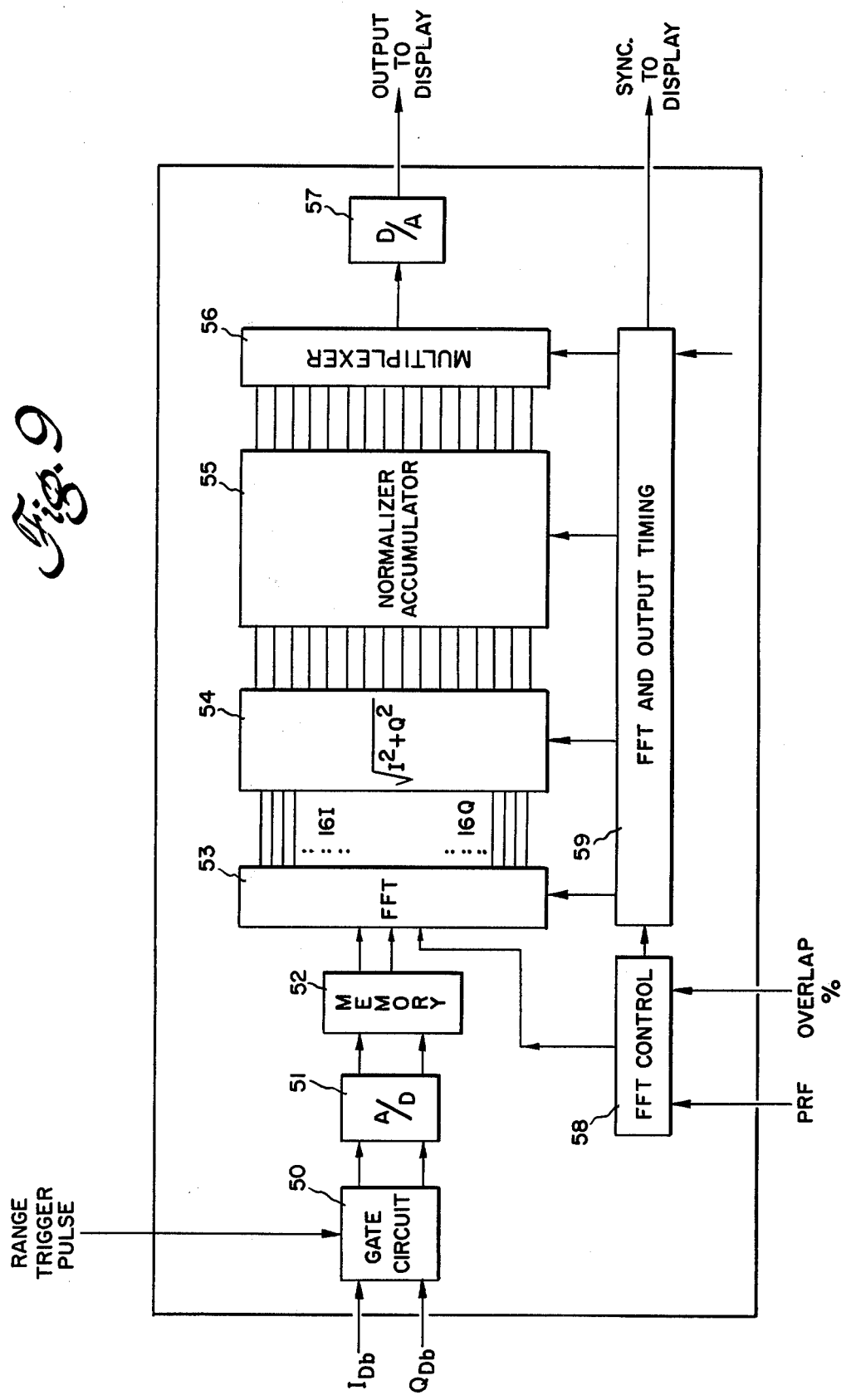

MEASUREMENT OF TRUE BLOOD VELOCITY BY AN ULTRASOUND SYSTEM

BACKGROUND OF THE INVENTION

This invention relates to a method and ultrasound apparatus for detecting liquid flow velocity, and more particularly to determining two components of velocity and the true flow vector using a steered beam scanner and a transducer array cross-beam technique.

Doppler systems which transcutaneously insonify the bloodstream with a single ultrasonic beam can provide accurate blood velocity measurements only if the direction of the velocity vector coincides with the direction of the beam; if these directions do not coincide it is necessary to know the angle $\theta$ between the velocity vector and the beam. Various methods have been suggested for deriving two components of velocity from which the true velocity vector is readily calculated, but many such methods require plural insonifying beams. The system described by P. A. Perronneau et al, Proceedings of the 2nd World Congress of Ultrasonics in Medicine, Rotterdam, The Netherlands, June 1973, pp. 259-266, utilizes two crystals angled toward one another and symmetrically located at one extremity of a B-scan probe diameter.

Blood velocity is detected by measuring the Doppler shifts in frequency imparted to ultrasound by reflection from moving red blood cells. Accuracy in detecting the Doppler shift at a particular point in the bloodstream depends on defining a small sample volume at the required location and then processing the echoes to extract the Doppler shifted frequencies. In order to be able to place an appropriately small sample volume at any desired location in the bloodstream and examine velocity in the major vessels, in the vicinity of heart valves or inside the heart chambers, a Doppler modality is incorporated in a real time sector scanning imaging system. The system provides electronic steering and focusing of a single acoustic beam and enables the user to illuminate a small sample anywhere in the field of view of the instrument, whose location can be visually identified on a two-dimensional B-scan image. A Fourier transform processor faithfully computes the Doppler spectrum backscattered from the sampled volume, and by averaging the spectral components the mean frequency shift can be obtained. Further explanation is given in copending, commonly assigned application Ser. No. 936,111, filed on Aug. 23, 1978, E. Papadofrangakis and W. E. Engeler, "Directional Detection of Blood Velocities in an Ultrasound System". This duplex system measures only the component of velocity parallel to the insonifying beam.

Using the visual orientation facility of the instrument, together with the beamsteering capability provided in the Doppler mode of operation, it is possible in certain situations to manually position the single acoustic beam available so that it coincides with the blood flow direction in at least one major artery, but in many cases the alignment cannot be achieved. A principal object of this invention is to measure the true blood velocity vector, independent of the orientation angle $\theta$, by suitably modifying the foregoing duplex instrument which has a single linear transmit-receive transducer array for both B-scan and Doppler modes.

SUMMARY OF THE INVENTION

A steered beam ultrasound instrument and a method of measuring the true flow velocity vector utilize the linear transducer array in a cross-beam configuration capable of resolving two orthogonal components of the velocity vector. The row of array elements is divisible into a transmitter sub-array and into left and right receiver sub-arrays whose location on either side of the center line is variable such that straight lines between any observation point in the field of view and the centers of the receive sub-arrays have equal angles with respect to a straight line between the observation point and the center of the transmitter sub-array; the backscattered center wave vectors then subtend the same angle at the observation point with respect to the transmitter wave vector. The transmitter elements are excited to sequentially generate pulses of ultrasound that propagate along a designated acoustic beam direction and insonify a sample volume of blood or similar liquid at the observation point. Left and right receivers are provided for coherently demodulating echo signals generated by receive elements with phase quadrature emission frequency reference signals and for time delaying and summing the echo signals to produce left and right focused in-phase (I) and quadrature (Q) signals. A computation circuit derives four Doppler processor input signals, I and Q inputs for the beam direction and for the transverse direction, realized by combining four signals representing the differences of the left and right focused I and Q signals and the sums of the left and right focused I and Q signals. A range gate extracts two pairs of analog samples from the Doppler signals after every ultrasound pulse transmission at a time corresponding to reception of exhoes backscattered from the same volume, and a dual channel Doppler processor computes from sets of analog samples the magnitude and sign of frequency shifts relative to the ultrasound emission frequency which correspond to two components of flow velocity parallel to and transverse to the beam direction. A vectorial sum of the two mutually perpendicular components is implemented to provide the true velocity vector.

The preferred embodiment is a duplex imaging system having a B-scan imaging and Doppler orientation mode and a subsequent Doppler mode, and is an electronically steered beam sector scanner into which the Doppler modality is incorporated with little added complexity. The system has a common transducer array of both modes. The focused I and Q signals are combined to form a resultant signal which is fed to the B-scan display device (a cathode ray tube), and sample volume for Doppler interrogation is identified. The location of the left and right receiver sub-arrays and the elements in each sub-aperture are selected by the system controller. The processing of received echoes in left and right groups of receiving channels is the same as for imaging except that in alternate pulse repetition intervals the phase of the demodulator reference signals is reversed by $\pi$ in either the left or right channel; this simple modification, without which only the differences of left and right focused I and Q signals can be obtained, enables calculation of the corresponding two sum signals. An interpolation filter is included in the Doppler signal computation circuitry to interpolate between the difference and sum signals in alternate pulse repetition intervals. The Doppler processor is preferably a real time digital Fast Fourier Transform processor. After a vector summer computes true velocity from the two components, the Doppler display prints out true bidirectional flow velocity vs. time and there may also be an oscilloscope so the user may observe the velocity variation in real time. An alternate method computes the transverse component as just described and the parallel component as in Ser. No. 936,111.

BRIEF DESCRIPTION OF THE DRAWINGS

FIG. 1 illustrates the linear transducer array cross-beam configuration and addition and subtraction of unit ultrasound wave vectors;

FIG. 2 is an enlarged view of a sample volume of blood showing a velocity vector and its components parallel to and perpendicular to the acoustic beam;

FIG. 3 is a sketch used in explaining the physical principle of Doppler velocity detection;

FIG. 4 shows the components of velocity which are measured and calculated by the cross-beam method;

FIG. 9 is a block diagram of one channel of the Doppler processor.

DESCRIPTION OF THE PREFERRED EMBODIMENTS

Figure 5:
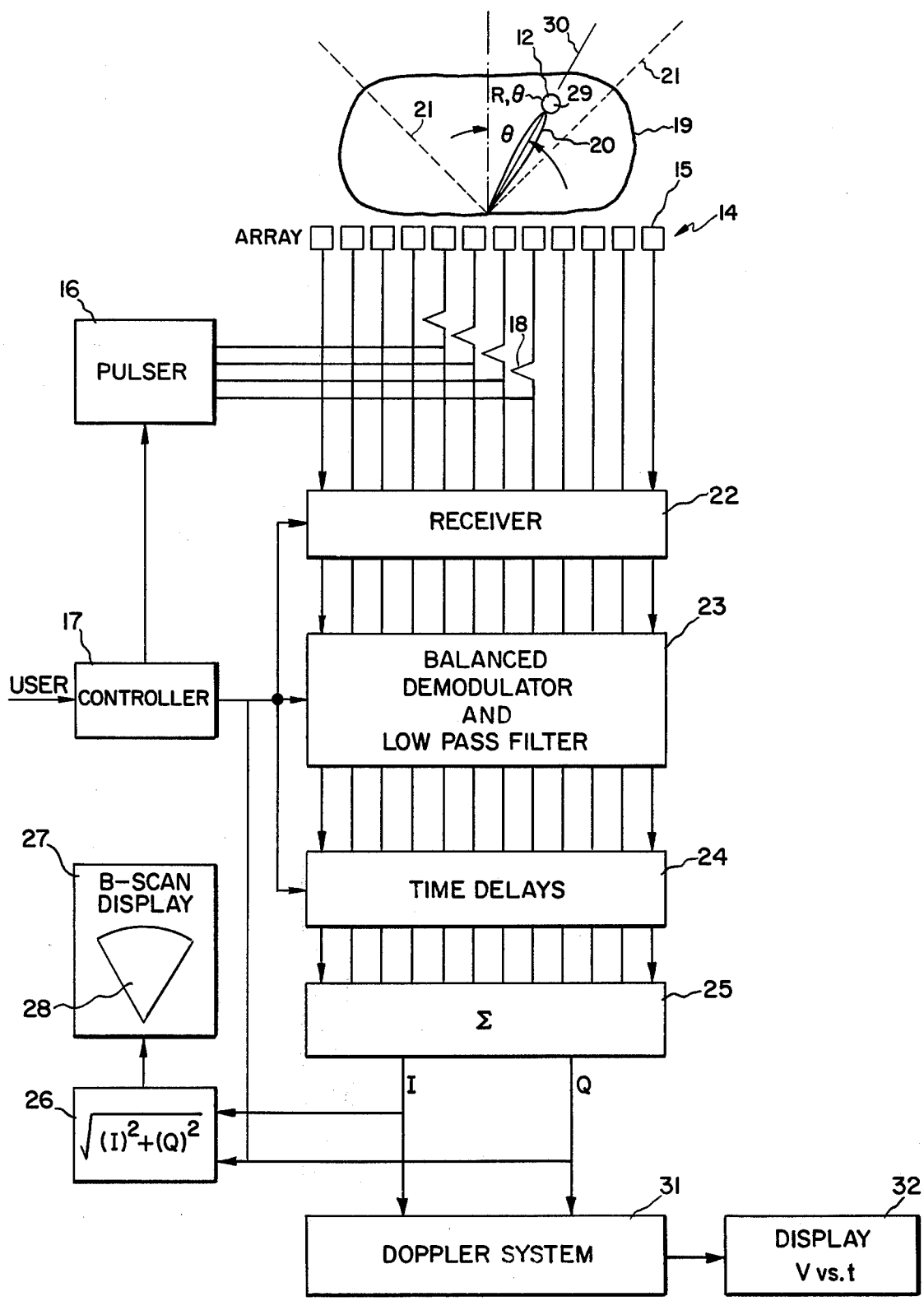
FIG. 5 is a simplified block diagram of a B-scan ultrasonic imaging system with which is incorporated a Doppler modality for blood velocity measurements.

The ultrasound system of measuring true blood velocity has a linear transmit-receive transducer array 10, FIG. 1, having a large number of equally spaced piezoelectric transducer elements 11. A cross-beam configuration of the array is capable of resolving two orthogonal components of the velocity vector. This approach utilizes a single ultrasonic transducer array, transmitting ultrasound from the center elements and receiving backscattered echoes from two sub-arrays defined by two sets of elements, on either side of the array centerline. The system in practice is capable of resolving the radial velocity component in the acoustic beamsteering direction and the transverse component at right angles to the beamsteering direction. The true flow vector can be accurately computed from these projections without prior knowledge of the orientation angle of the acoustic beam.

The following description assumes a knowledge of a steered beam or phased array imager for making wide angle sector scans. The transmit sub-array T is made of the center twenty or so elements of transducer array 10 which are individually excited in linear time sequence to transmit an acoustic beam steered in the direction $\theta$ and focused at range R, where R=OA. The angle $\theta$ is measured from a normal to the array which passes through its midpoint O, and $\theta$ and R have been selected previously by the user by consulting the B-scan display. In reception, echoes backscattered from red blood cells moving past observation point A are received by left and right receiver sub-arrays $R_L$ and $R_R$, defining two sub-apertures on either side of the beamsteering direction or either side of the array midpoint O. The left and right receiver sub-arrays are each made of about ten adjacent transducer elements, and are located such that straight lines between observation point A and the centers of the two receiver sub-arrays have equal angles, $\phi$, with respect to a straight line between the observation point and the center, O, of the transmitter sub-array. This relationship, that the angles $\phi$ are equal, is maintained for every observation point in the field of view, necessitating that the left and right receiver sub-arrays are variably located depending upon the particular observation point at which the true flow velocity vector $\vec{v}$ is being detected. The left and right subsets of receive elements are selected by blanking those receiving channels that are to be inactive. A receiver sub-array specification schedule is prepared for every separate observation point within the sector being scanned, giving in each case the center element and total number of elements in the two sub-arrays. This may be done only once and is entered into the system controller for the Doppler mode of operation. The transmitter aperture will in all cases comprise the same number of elements.

In FIG. 1, $\vec{K_0}$ is a unit vector in the direction of the transmitted ultrasound wave vector, and $\vec{K_1}$ and $\vec{K_2}$ are unit center ultrasound wave vectors for the two receiving directions. The position of the center element in left and right receiver sub-arrays $R_L$ and $R_R$ must be such that the center wave vectors $\vec{K_1}$ and $\vec{K_2}$ subtend the same angle $\phi$ at point A with respect to the transmitter wave vector $\vec{K_0}$. In oreder to understand the mathematical basis of the invention, it is helpful to review vector summation and subtraction by the parallelogram method. If two adjacent sides of the parallelogram drawn below point A are the received center wave vectors $\vec{K_1}$ and $\vec{K_2}$, and the angle between is $2\phi$, then the vector sum $\vec{K_1}+\vec{K_2}$ is along the beamsteering direction, and the vector difference $\vec{K_1}-\vec{K_2}$ is perpendicular to the beamsteering direction.

FIG. 2 is an enlarged view of a sample volume of blood 12 and of the red blood cells 13 in the blood stream which are very small (about 8 microns in diameter) as compared to the ultrasound wavelength. The red blood cells move with a certain true mean volocity $\vec{v}$ that is at an angle $\theta$ to the direction of incident ultrasonic energy along the beam direction or scan line. Echoes backscattered from the red blood cells are frequency shifted by an amount proportional to the frequency of the incident wave and the velocity of blood flow. Movement of red blood cells through the sample volume toward the transducer array compresses the wavelength of the reflective wave, increasing the frequency, and movement of red blood cells away from the transducer array lengthens the wavelength of the reflective wave, decreasing the frequency. This instrument measures the two components of true flow velocity parallel to the beam direction, $\vec{v_b}$, and transverse to the beam direction, $\vec{v_t}$. The red blood cell population of sample volume 12 is constantly changing and it is necessary to get a number of samples of frequency shifted echoes in order to calculate an accurate value of true velocity. Another factor is that blood flow may be turbulent and a broad distribution of velocities may be present in the sample volume, and in general the velocity vectors are oriented in many directions. The present system has the capability of detecting a distribution of blood velocities, but the discussion is simplified by assuming the true flow velocity has only one direction. The system also measures the velocity of similar liquids containing small particles capable of backscattering echoes.

The physical principle involved in Doppler velocity detection is shown in FIG. 3. If scatterers (in this case red blood cells) move with velocity $\vec{v}$ past a sample volume in the insonified field of view, the rate of change of path length from transmitter to receiver is given by the dot product of incident and backscattered ultrasound wave vectors and the velocity $\vec{v}$. The change in path length imparts a Doppler frequency shift $\Delta\omega$ at the receiver given by $$\Delta\omega = (\vec{K_1} - \vec{K_0}) \cdot \vec{v} \tag{1}$$

Since the directions of the transmitted and received wave vectors are at any instance fixed by the transducer geometry, the detected Doppler shift indicates a single component of the particle velocity vector. In the case of a transcutaneous B-scan transducer transmitting and receiving ultrasound from the same direction (T and R at the same location), the frequency shift reduces to the more familiar expression $$\Delta f = 2 f_0 v \cos \theta / c \tag{2}$$

where $f_o$=emission frequency, c=ultrasound propagation speed (1540 m/sec for tissue), and $\theta$ is the orientation angle. Referring to FIG. 1, if blood is flowing past point A in the direction of vector $\vec{v}$, the change of path length between the transmitter and each of the two receive sub-apertures will be $$(\vec{K_2} + \vec{K_0}) \cdot \vec{v} \text{ and } (\vec{K_1} + \vec{K_0}) \cdot \vec{v} \tag{3}$$

The difference $(\vec{K_2} - \vec{K_1}) \cdot \vec{v}$ yields the transverse component of velocity, i.e., the component at right angles to the beam direction. The sum $(\vec{K_1} + \vec{K_2}) \cdot \vec{v} + 2\vec{K_0} \cdot \vec{v}$ results in a component of velocity along the beam direction. The transverse component of velocity is given by $$v_t = \frac{(\vec{K_2} - \vec{K_1}) \cdot \vec{v}}{2 \sin \phi} \tag{4}$$

and the beam direction component by $$v_b = \frac{(\vec{K_1} + \vec{K_2}) \cdot \vec{v} + 2\vec{K_0} \cdot \vec{v}}{2 \cos \phi + 2} \tag{5}$$

The basic approach of the cross-beam method for detecting the true velocity vector $\vec{v}$, implemented with a single linear transducer array which transmits a single ultrasonic beam, is further clarified in FIG. 4. The sample volume of blood through which the true flow velocity is being measured is located at point A. The system detects left and right components of velocity $\vec{v_L}$ and $\vec{v_R}$, that is, the components along the left and right received center ultrasound wave vectors. Given $\vec{v_L}$ and $\vec{v_R}$, the system computes $\vec{v_b}$ and $\vec{v_t}$, the components parallel to and transvers to the beam direction. Given $\vec{v_b}$ and $\vec{v_t}$, the system computes v, the desired result.

The preferred embodiment is the duplex imaging system in FIG. 5 which is a real time single-sector steered beam scanner with an incorporated Doppler modality for real time bidirectional true blood flow velocity measurement. There are two modes of operation of the duplex system for velocity measurements: (a) the B-scan imaging and Doppler orientation mode and (b) the Doppler processing and display mode. The latter modality is always subsequent to the former and the two are never simultaneous. The same transducer array is used for imaging and velocity detection and is the key to increased accuracy as compared to prior art instruments. Common linear transducer array 14 constructed of piezoelectric elements 15 has a larger interelement spacing for receive than for transmit to yield a wide aperture system with low side lobe artifacts using a minimum number of relatively expensive receiver channels. The transmit array is at the center of a larger receive array (elements in the center function dually as transmit and receive elements), and the transmit elements are associated with a pulser 16 capable of generating single impulses for B-scan operation so as to produce wide bandwidth ultrasound pulses, and multiple impulses for Doppler operation having a frequency equal to the required emission frequency (2–5 MHz) so as to generate narrow bandwidth ultrasound pulses. The repetition frequency of multiple impulse excitation is variable and has high, intermediate, and low settings selected by a controller 17 with user inputs.

During successive transmission periods of the B-scan mode, pulser 16 generates a series of excitation impulses 18, one per transmit element, with a time delay between successive impulses that is incremented from one transmission period to the next to thereby transmit wide bandwidth pulses of ultrasound along many different scan lines covering the region of a body 19 being examined. A single acoustic beam 20 at an angle $\theta$ from the normal is illustrated and a total sector scan angle of approximately 90° is indicated by dashed lines 21. During alternate reception periods, the received echo signals caused by energy echoing from various body structures and detected by receive elements in common array 14 are individually amplified and fed to echo processing channels. The receiving channels feature the use of base band signal processing to achieve good lateral resolution while greatly reducing the required time delay accuracy and instead requiring more easily achievable phase focusing accuracy, and have as major components a receiver 22, a balanced demodulator and low pass filter 23, a time delay device 24 such as a delay line, and a pair of summers 25. In practice, three receiver system parameters are varying during the course of an echo reception period, these being the time delay between elements, the reference signal of the balanced demodulators, and also the receive aperture width. The outermost receiving channels are blanked progressively at shorter ranges to reduce the receive aperture by steps and realize improved lateral resolution near the skin. For B-scan operation, the summed and focused in-phase (I) and quadrature (Q) signals are further processed in circuit 26 to derive a resultant signals obtained by squaring the I and Q components, adding together the squared signals and taking the square root of the sum. The resultant is the video signal and it is post-processed to improve the image before being fed to cathode ray tube 27 as the Z control or to control the electron beam intensity. Sector-shaped image 28 is built up radial scan line by radial scan line as the transmitted beam direction is changed incrementally, and is a two-dimensional picture of a planar slice through the body which is displayed in real time.

The Doppler orientation mode involves visual observation of B-scan image 28 by the physician to identify a relatively small sample volume within the heart or closeby great arterial vessels through which the true bidirectional velocity of blood flow (i.e., the magnitude and direction toward or away from the transducer array) is to be measured. A suitable landmark on the image delineates the Doppler examination region, such as by illuminating the beam direction through the sample volume and by an illuminated range cursor. Assume for instance that a sample volume 29 is being examined (top of FIG. 5) which is along scan line 30 at an angle $\theta$ to the normal and which has a range R.

In the Doppler mode of operation, system controller 17 is set by the user such that narrow bandwidth pulses of ultrasound are transmitted only along the chosen scan line intersecting the sample volume, and range gating is employed to sample echoes from the desired depth and detect velocity patterns at specific locations. Repetitive pulsing of the transmitter elements at the frequency equal to the required emission frequency causes the response bandwidth of the transducer to be narrowed. See copending, commonly assigned application Ser. No. 936,115 filed on Aug. 23, 1978, E. Papadofrangakis, J. A. Fakiris, W. E. Engeler, "Duplex Ultrasonic Imaging System with Repetitive Excitation of Common Transducer in Doppler Modality". By an appropriate timing of the beginning of the multiple pulsing of each element (time delay increments are the same as for single impulse excitation), the transmitted ultrasound beam is steered to a certain direction or can be focused at a certain point in space. Another feature of the Doppler modality transducer excitation is variable repetition intervals for the multiple excitation in order to be able to adequately sample, at various ranges, backscattered echoes from slow as well as fast moving blood cells. The instrument being described has pulse repetition frequency (PRF) settings of 4 KHZ, 8 KHz, and 16 KHz. For high values of velocity flow in sample volumes at close ranges, detection is accomplished by using a 16 KHz PRF. The velocity resolution is relatively poor. Superior velocity resolution at low flow velocities and long ranges is achieved by the 4 KHz PRF. To provide additional flexibility in the choice available to the user, there is an intermediate setting of 8 KHz PRF. The chosen PRF (ultrasound pulse repetition frequency) values in the Doppler mode are considerably higher than those provided in imaging, and the transmitter subsystem is capable of providing appropriate excitation intervals for both modes of operation.

On receive, the aperture specification schedule used in normal B-scan operation to activate the appropriate number of elements 15 compatible with range and resolution requirements, is utilized to split the array into left and right receiver sub-arrays. Controller 17 is suitably a microprocessor that is programmed to provide the position of each sub-aperture center active element, as well as the width or number of elements of the sub-aperture. The latter is determined by a method similar to one employed in the normal imaging mode for the entire array. The received echo signals are processed through the quadrature receiving channels and electronically steered and dynamically focused in much the same manner as for B-scan imaging, with the exceptions to be explained in detail later. The left and right sub-array focused I and Q signals are fed directly to a Doppler system 31 without generating their resultant. Full details of the Doppler system are given in FIGS. 7–9. After computing the two orthogonal components of flow velocity, the magnitude and direction (toward or away from the transducer array) of true flow velocity are presented in real time to a Doppler display 32 for visual observation by the physician. The echo processing channels are described briefly here, and further information is given in U.S. Pat. No. 4,155,260, granted May 22, 1979, W. E. Engeler and J. J. Tiemann, "Ultrasonic Imaging System", assigned to the same assignee, the disclosure of which is incorporated herein by reference. One of the features of this invention is that the additional hardware required to implement this concept involves an already existing switch, which alters the phase of half of the receiving elements of the array by $\pi$ in alternate pulse repetition intervals.

Figure 6:
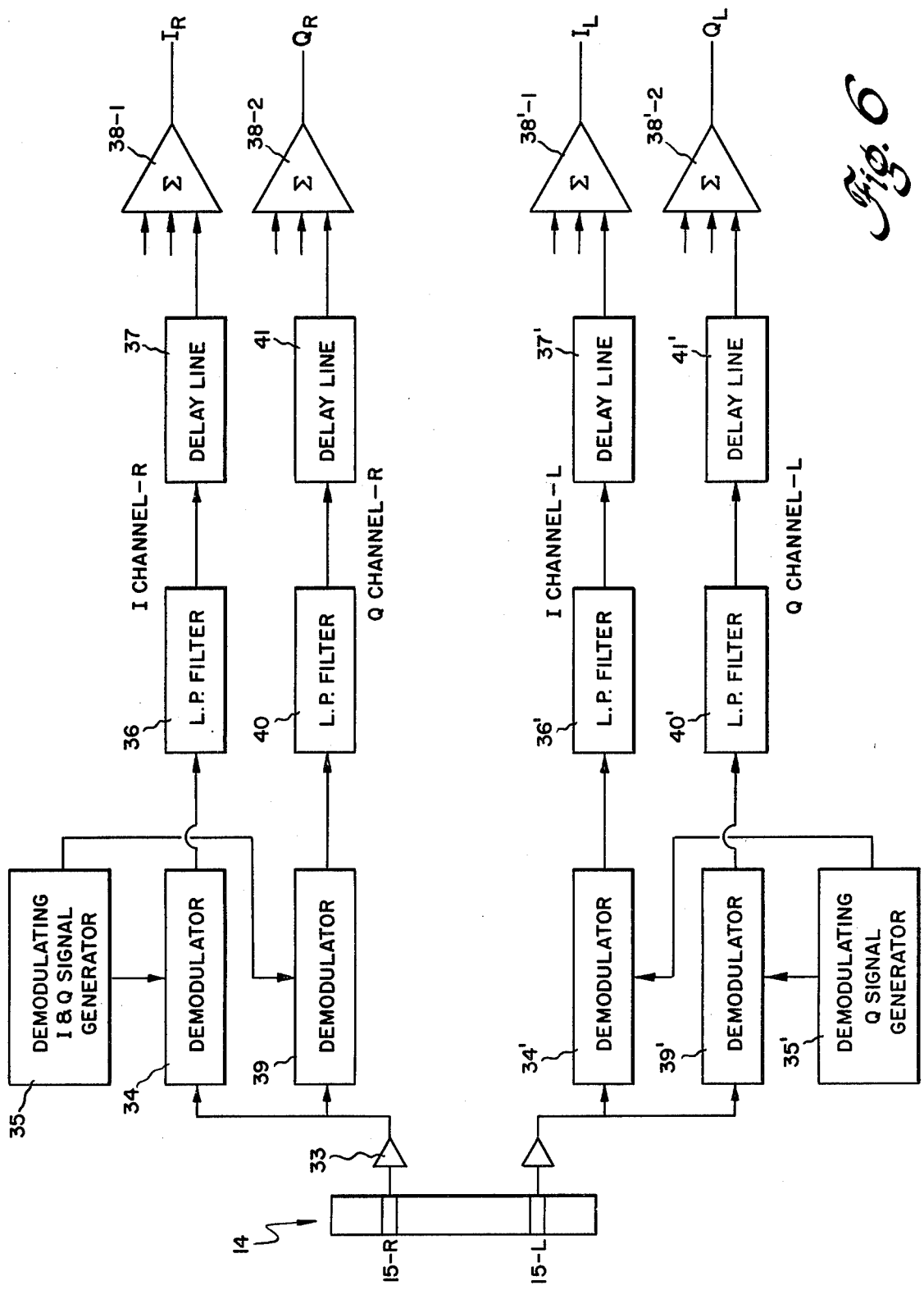
FIG. 6 gives further details of the left and right in-phase (I) and quadrature (Q) receiving channels.

Referring to FIG. 6, the I and Q processing channels for echo signals generated by single left and right receive elements 15-L and 15-R are depicted in greater detail. The echo signal generated by 15-R passes through a preamplifier 33 to an I channel demodulator 34 where it is mixed with a demodulating signal from generator 35 which has a fundamental frequency equal to the resonant frequency of the transducer element or equal to the ultrasound emission frequency. The demodulating reference signal further has a phase determined by the path length difference to the object point under examination. The demodulated signal is passed through a low pass filter 36 to recover the envelope and then is fed to a delay line 37 which is preprogrammed with the steering delays and, in the situation where the path lengths differ sufficiently, a coarse focusing delay proportional to the path length difference. The delayed focused demodulated signal is fed to a summing amplifier 38-1 where it is coherently summed with all the other right I channel delayed demodulated signals to give the focused in-phase signal $I_R$. The demodulating signal utilized in each of the right Q channels is set to be in phase quadrature relationship with respect to the I channel demodulating signal. The received echo is fed in parallel to demodulator 39 and mixed with a phase quadrature emission frequency reference from generator 35 which is further set lagging in phase with respect to the echo signal by the same phase displacement existing in connection with the echo and demodulating signals in the I channel. The quadrature demodulated signal similarly is passed through low pass filter 40 to recover the envelope, is steered and time delay focused in delay line 41, and then fed to summing amplifier 38-2 to be coherently summed with the delayed, focused demodulated signals from other right-hand Q channels to yield the focused quadrature signal $Q_R$. Corresponding components of the left group of receiving channels for processing the received echoes from element 15-L are designated by corresponding primed numerals; these channels generate left focused in-phase and quadrature signals $I_L$ and $Q_L$.

Figure 7:
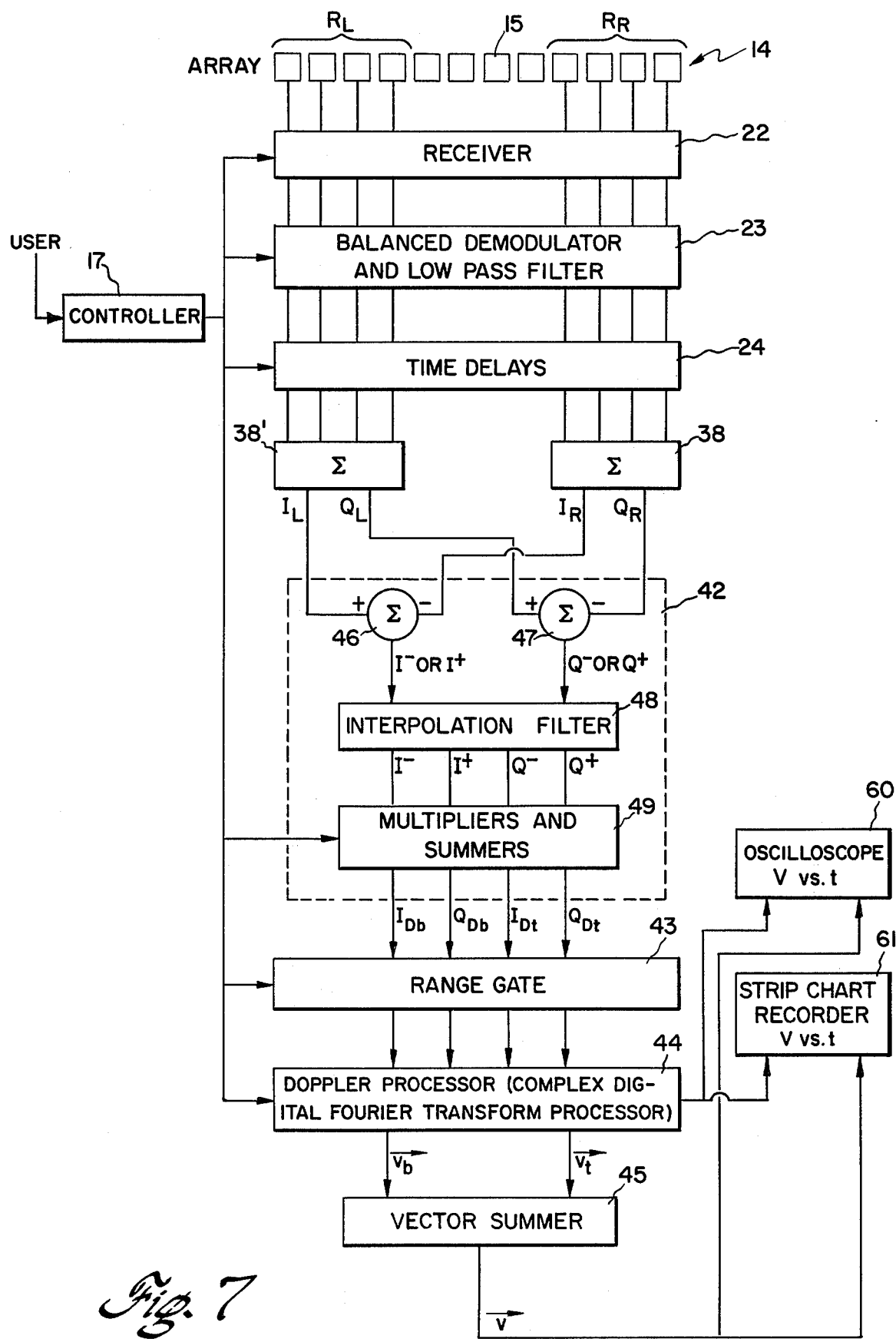
FIG. 7 is a block diagram of the receiver and Doppler sub-system for calculating and displaying the true blood velocity by the cross-beam technique.
Figure 8:
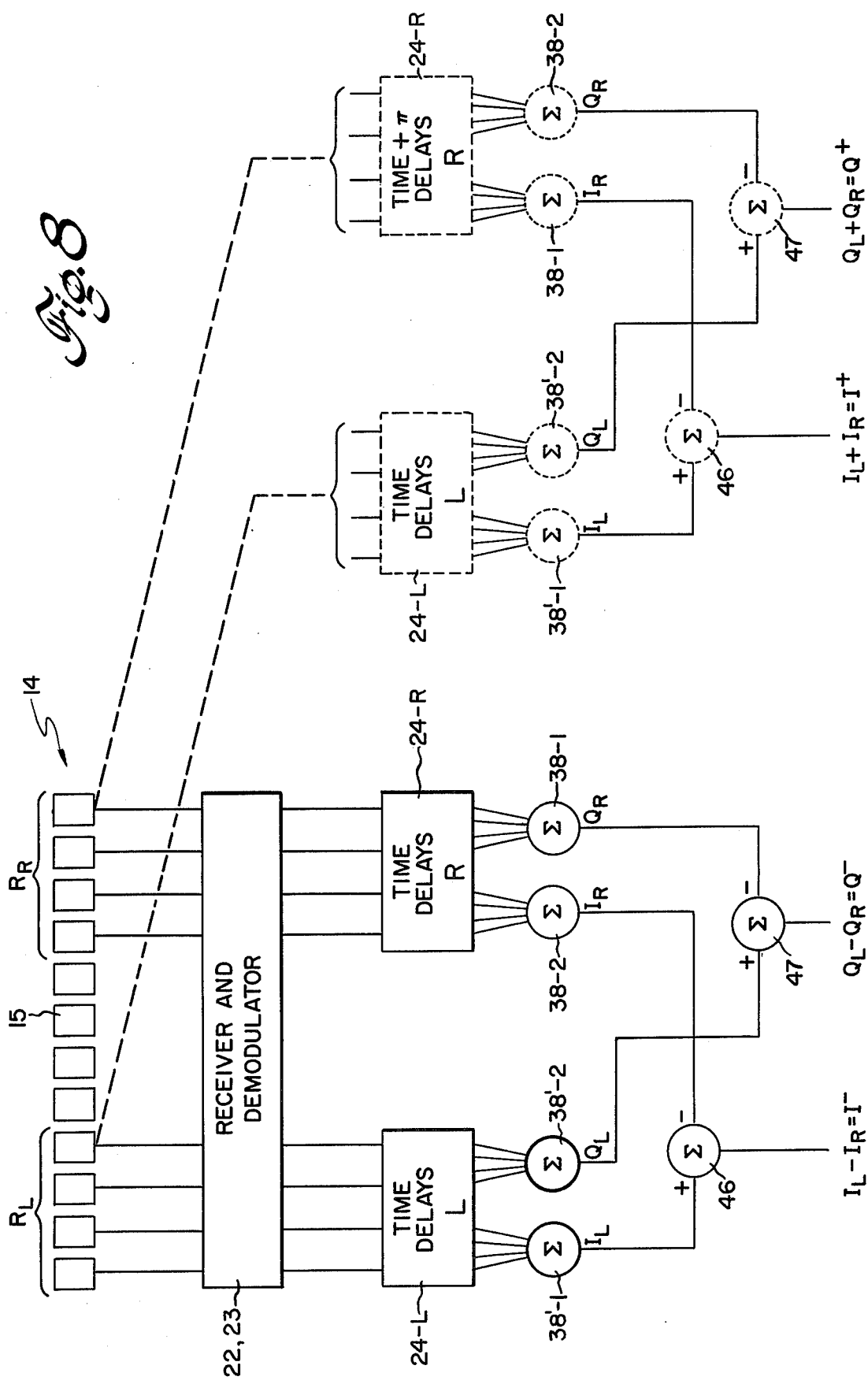
FIG. 8 shows schematically in greater detail the receiving channel circuitry for obtaining the differences and sums of the focused echo signals for the left and right receiver sub-arrays.

FIG. 7 incorporates system block diagrams for the Doppler system and display. A Doppler signal computation circuit 42 (enclosed by dashed lines) computes in-phase and quadrature Doppler processor input signals for the beam direction, $I_{Db}$ and $Q_{Db}$, and for the transverse direction, $I_{Dt}$ and $Q_{Dt}$, from combinations of the left focused in-phase and quadrature signals, $I_L$ and $Q_L$, and the right focused in-phase and quadrature signals, $I_R$ and $Q_R$. The mathematical derivation and computational steps are given subsequently. The Doppler input signals are sampled at a specific time after each transducer excitation interval which corresponds to the time taken for the ultrasonic signal to return to the transducer from range R. A range gate 43 is opened by controller 17 for a relatively short interval at a time corresponding to reception of echoes backscattered from sample volume 29 and extracts two pairs of analog samples in parallel. Doppler processor 44 has dual channels, one for the pair of beam direction analog samples and the other for the pair of transverse direction analog samples, and embodies a complex arithmetic implementation of the Fourier transform and is preferably a real time digital Fast Fourier Transform (FFT) processor. The parallel channels compute the components of velocity parallel to and transverse to the beam direction, $v_b$ and $v_t$, from sets of pairs of analog samples. The true flow velocity vector v is realized at the output of a vector summer 45.

In computation circuit 42, the focused in-phase and quadrature signals from receiver sub-arrays $R_L$ and $R_R$, one on either side of the center line, are subtracted in a difference network to provide difference signals $$I^- = I_L - I_R$$

and $$Q^- = Q_L - Q_R \qquad (6)$$

It can be shown mathematically that in order to extract $\vec{v_b}$, one must apply to the input of one channel of the Doppler processor, an in-phase Doppler signal $$I_{Db} = \tfrac{1}{4}[I^+Q^+ - I^-Q^-] \qquad (7)$$

where:

$$I^+ = I_L + I_R$$

and $$Q^+ = Q_L + Q_R \qquad (8)$$

Similar combinations of the four in-phase and quadrature difference and sum signals are necessary to derive a suitable quadrature signal $Q_{Db}$ for input to the Doppler processor, as follows:

$$Q_{Db} = \tfrac{1}{4}[Q^{+2} - Q^{-2} + I^{+2} - I^{-2}] \qquad (9)$$

In order to extract $\vec{v_t}$, the appropriate combinations of the difference and sum signals are:

$$I_{Dt} = -\tfrac{1}{4}[I^+Q^- - I^-Q^+] \qquad (10)$$

$$Q_{Dt} = \tfrac{1}{4}[Q^{+2} - Q^{-2} - I^{+2} + I^{-2}] \qquad (11)$$

The B-scan steered beam imager as previously described automatically provides the two difference signals, $I^-$ and $Q^-$, with the addition of two summing circuits 46 and 47, one for realizing the difference $I_L - I_R$ and the other the difference $Q_L - Q_R$. The sum signals $I^+$ and $Q^+$ are obtained by reversing the phase of the balanced demodulator reference signals by $\pi$ in alternate ultrasound pulse repetition intervals (PRI). The demodulating references are generated by elements 35 and 35' in FIG. 6, and one of these, either the left channel or the right channel, is changed by 180° in alternate PRIs. Means for implementing this phase change already exists in a system constructed in accordance with FIG. 5 of U.S. Pat. No. 4,155,260, and an appropriate switch is available (in elements 71, 77, and 78) to initiate this action. Operation of the computation circuit to derive difference signals $I^-$ and $Q^-$ in one PRI is depicted in full lines at the left of FIG. 8. The dashed line showing for the next PRI at the right of FIG. 8 assumes that the balanced demodulator reference signals for the I and Q channels in the right group of receiving channels, for processing the echo signals from right receiver sub-array $R_R$, are shifted by $\pi$. Summing circuits 46 and 47 then generate $I_L + I_R$ and $Q_L + Q_R$. In practice, the two difference signals and the two sum signals are required in each ultrasound pulse repetition interval. For this purpose, a digital interpolation filter 48 accepts the outputs of summing circuits 46 and 47 and interpolates between values of $I^+$ and $Q^+$ from alternate PRIs. The filter also interpolates between values of $I^-$ and $Q^-$ in the other set of alternate PRIs. Computation of in-phase and quadrature Doppler signals for the beam direction, $I_{Db}$ and $Q_{Db}$, and of the in-phase and quadrature Doppler signals for the transverse direction, $I_{Dt}$ and $Q_{Dt}$, is achieved by networks of multipliers and summers 49. The four different combinations of the two sum signals and two difference signals that are required are given in equations (7), (9), (10), and (11). The operation of range gate 43 to extract in parallel four analog samples of the Doppler signals for a relatively short interval at a time corresponding to reception of echoes backscattered from the sample volume through which the true flow velocity vector is being measured, has been explained.

The separate channels of dual channel Doppler processor 44 are fully described in copending, commonly assigned application Ser. No. 936,111, filed on Aug. 23, 1978, E. Papadofrangakis and W. E. Engeler, "Directional Detection of Blood Velocities in an Ultrasound System". FIG. 9 is a block diagram of the preferred embodiment of the Doppler processor for the beam direction in-phase and quadrature Doppler input signals. This sub-system extracts a Doppler frequency spectrum from sixteen such Doppler signals, computes the power spectrum and generates an analog output that represents sixteen Doppler frequencies. Half of these frequencies correspond to positive Doppler shifts (forward flow) and the other half to negative shifts (receding flow). The processor operates in real time with the system running at pulse repetition frequencies of 4 KHz, 8 KHz, and 16 KHz. When processing time is available, particularly at higher pulse repetition frequencies, the processor integrates several spectra before reporting results. The processor can operate on data samples in one of two ways resulting in either a block or a sliding transform.

Gate or sampling circuit 50 corresponds to range gate 43 and has a sampling interval that is very short, such as 0.1 microseconds, as compared with the time duration of the ultrasound pulse to realize velocity measurements with maximum sensitivity at a specific point in the bloodstream. Upon the occurrence of a range trigger pulse, gate circuit 50 passes a pair of analog samples to analog-to-digital converter 51 and the pairs of digitized samples are stored in a memory 52. Doppler processor 53 features a digital implementation of a sixteen-point real time Fast Fourier Transform. The number of transform points is determined by the minimum desirable spectral resolution and a tradeoff of range and velocity discrimination. FFT 53 is constructed with eight CE chips such as are disclosed and claimed in U.S. Pat. No. 4,020,334, N. R. Powell ad J. M. Irwin, "Integrated Arithmetic Unit for Computing Some Indexed Products", assigned to the assignee of this invention, the disclosure of which is incorporated herein by reference. These CE chips provide complex arithmetic for a sixteen-point digital FFT based on a radix 4 algorithm. The digital FFT computation gives an ordered output frequency spectrum comprising sixteen frequency bins, half of which correspond to positive Doppler shifts and the other half to negative shifts. An output spectrum can be calculated once sixteen I and sixteen Q samples form sixteen consecutive echo returns are accumulated in memory 52. These samples are Fourier transformed to produce sixteen real and sixteen imaginary coefficients, and the power spectrum is obtained by squaring and adding the coefficients on a 1:1 basis. Movement of the red blood cells causes rotation of an I-Q phasor in a unit circle. The rate of rotation indicates velocity, direction of rotation gives flow sense. It is a property of the Discrete Fourier Transform (DFT) that contradirected velocities produce complex output numbers corresponding to different velocity bins. In this way, a complex arithmetic Fourier transform permits a separation of the Doppler spectra for forward or receding flow.

The outputs of FFT processor 53 are sixteen I and sixteen Q signals representing frequency shifts, and sixteen resultant signals are generated for display in circuit 54 by squaring corresponding I and Q signals, adding the squares and taking the square root of the sum. The sixteen resultant signals, half for forward flow and half for receding flow, are fed to an accumulator normalizer 55 for presentation to the display either in block transform mode or sliding transform mode. In the first exclusive sets of analog sample pairs are analyzed, i.e., pulse-echo cycles 1-16, 4-20, 8-24, etc. In the latter mode overlapping sets of analog sample pairs are analyzed, i.e., pulse-echo cycles 1-16, 4-20, 8-24, etc. Video output data passes through a multiplexer 56 where it is multiplexed with an ECG signal, and is then fed to a digital-to-analog converter 57 to generate the output data. Input commands for the control units come from controller 17. Block 58 is the FFT control and its inputs are a transform slide number command and a velocity scaling command, and block 59 is FFT and output timing circuitry. At each instant in time, the Doppler processor reports the ultrasound power spectra backscattered from the sample volume, and this corresponds to the velocity distribution in the volume. The distribution contains eight positive and eight negative readings, and one may average the velocity components present in the sample volume and realize a mean velocity reading for one component of velocity.

The duplex imaging system has two types of Doppler mode display devices for the true flow velocity vector information calculated by vector summer 45, FIG. 7. The bidirectional true flow velocities are first displayed on an oscilloscope 60 so that the user can observe their variation in real time. A hard copy of the evolution of the true blood velocities with time is printed up by a strip chart recorder 61. The recorder plots the information at a rate selected at the start, and most of the display period is taken up by the Doppler information with the smaller portion reserved for a multiplexed ECG signal. The latter provides a time reference for events occurring during the course of a heart cycle.

An alternative way of measuring two components of velocity parallel to and transverse to the beam steering direction is to get the transverse component as just described while the parallel component is detected as taught in Ser. No. 936,111. The latter method does not require that the transducer array be divided into left and right sub-arrays for reception; instead the entire array is the receive array with the exception that near the skin the receive aperture is reduced for improved imaging. The B-scan imaging mode focused I and Q echo signals, FIG. 5, are fed directly to a single channel Doppler processor as shown in FIG. 9. The range gate extracts a pair of analog signals after every pulse transmission, and once sixteen pairs of samples are accumulated the processor computes sixteen resultant signals representing frequency shifts and therefore velocity along the beam-steering direction. The true flow velocity vector is not computed in real time; the two components are obtained sequentially and are stored for presentation to the vector summer.

The invention can be practiced with other types of B-scan sector scan imagers whose details differ from those just given. Synchronous demodulation of the echo signals with phase quadrature emission frequency references is an essential feature of the signal processing, but phase focusing is not essential. This invention makes it possible to utilize the software and hardware flexibility of such systems to establish a cross-beam configuration, by utilizing a single linear transducer array. A minimum of additional hardware is introduced to derive and correlate the velocity components sensed by each beam, to readily identified blood flow directions with respect to the transducer. This ultrasound technique is a strictly noninvasive, nontraumatic method for measuring the true blood flow velocity vector.

While the invention has been particularly shown and described with reference to preferred embodiments thereof, it will be understood by those skilled in the art that various changes in form and details may be made therein without departing from the spirit and scope of the invention.

The invention claimed is:

1. A steered beam ultrasound instrument for measuring two components of the flow velocity of blood and similar liquids comprising:
    a linear transducer array for transmitting pulses of ultrasound with a preselected emission frequency and for generating received echo signals,
    said array being comprised of a row of elements divisible into a transmitter sub-array and into left and right receiver sub-arrays that are variably located such that received center wave vectors through any observation point in the field of view subtend approximately equal angles with respect to a transmitter wave vector through the observation point,
    means for exciting the elements of said transmitter sub-array to sequentially generate ultrasound pulses that propagate along a designated beam direction and insonify a sample volume through which the true flow velocity vector is being determined,
    left and right receiver means for coherently demodulating echo signals generated by the respective sub-arrays with phase quadrature emission frequency references and for producing left and right focused in-phase and quadrature signals,
    computation means for deriving in-phase and quadrature Doppler signals for the beam direction and for the transverse direction realized by combining four signals representing the differences of the focused left and right in-phase and quadrature signals and the sums of the focused left and right in-phase and quadrature signals,
    a range gate for extracting analog samples from said Doppler signals after every pulse transmission at a time corresponding to reception of echoes backscattered from the sample volume, and a Doppler processor for deriving from sets of said analog samples two components of flow velocity parallel to and transverse to the beam direction.

2. The ultrasound instrument of claim 1 further including means for vectorially summing the two components of velocity to realize the true flow velocity vector.

3. The ultrasound instrument of claim 2 wherein said Doppler processor is a real time digital Fast Fourier Transform processor.

4. The ultrasound instrument of claim 1 wherein said computation means for deriving Doppler signals is comprised of circuitry for producing two difference signals representing the differences of the left and right focused in-phase and quadrature signals and two sum signals representing the sums of the left and right focused in-phase and quadrature signals, and circuitry for combining said difference and sum signals to obtain two in-phase and two quadrature Doppler signals.

5. The ultrasound instrument of claim 4 wherein one of said left and right receiver means for coherently demodulating echo signals with phase quadrature references is operative to shift the phase of the references by $\pi$ in alternate ultrasound pulse repetition intervals, and wherein said computation means includes an interpolation filter at the output of the circuitry for producing two difference and two sum signals.

6. A steered beam ultrasound instrument for measuring the true flow velocity of blood and similar liquids comprising:

a linear transducer array comprised of a row of transducer elements divisible into a central transmitter sub-array and into left and right receiver sub-arrays that are variably located such that straight lines between any observation point in the field of view and the centers of said receiver sub-arrays have equal angles with respect to a straight line between the observation point and the center of said transmitter sub-array, transmitter means for exciting the transmitter sub-array elements to sequentially generate pulses of ultrasound with a preselected emission frequency that propagate along a designated beam direction and insonify a sample volume through which the true flow velocity vector is being determined, left and right receiver means for coherently demodulating received echo signals, generated by the elements of the respective sub-arrays, with phase quadrature emission frequency reference signals and for time delaying and summing the demodulated signals to produce focused in-phase and quadrature signals for both the left and right sub-arrays, a Doppler signal computation circuit for deriving two difference signals representing the differences of the left and right focused in-phase and quadrature signals and two sum signals representing the sums of the left and right focused in-phase and quadrature signals, and for combining said four sum and difference signals to produce in-phase and quadrature Doppler processor input signals for the beam direction and for the transverse direction, a range gate for extracting analog samples from said Doppler signals after every pulse transmission at a time corresponding to reception of echoes backscattered from the sample volume, a Doppler processor embodying a complex arithmetic implementation of the Fourier Transform for deriving from sets of said analog samples two components of flow velocity parallel to and transverse to the beam direction, and means for vectorially summing the two components of flow velocity to realize the true velocity vector.

7. The ultrasound instrument of claim 6 wherein one of said left and right receiver means for coherently demodulating echo signals with phase quadrature reference signals has provision for shifting the phase of the reference signals by $\pi$ in alternate ultrasound pulse repetition intervals, and an interpolation filter through which the two difference and two sum signals pass before being combined.

8. The ultrasound instrument of claim 6 wherein said complex Fourier Transform processor operates in real time at plural pulse transmission repetition frequencies and is a sixteen-point Fast Fourier Transform processor.

9. The ultrasound instrument of claim 8 further including display means for visually displaying true bidirectional velocity as a function of time.

10. A duplex ultrasonic imaging system having a B-scan and Doppler orientation mode of operation and a subsequent Doppler mode of operation comprising:

a common linear array of transducer elements for both modes for transmitting pulses of ultrasound with a preselected emission frequency and for generating received echo signals, means for exciting selected elements during B-scan operation to sequentially generate ultrasound pulses that propagate along different beam directions to perform a sector scan of a region being examined, means for coherently demodulating said echo signals using phase quadrature emission frequency references and for time delaying and summing the demodulated signals to produce a focused in-phase and a focused quadrature signal, means for deriving a resultant signal from said focused in-phase and quadrature signals, and a B-scan display for displaying the resultant signals as a visual image of the insonified region, said linear array during Doppler operation being divisible into a transmitter sub-array and into left and right receiver sub-arrays that are variably located such that straight lines between any observation point in the field of view and the centers of said receiver sub-arrays have equal angles with respect to a straight line between the observation point and the center of said transmitter sub-array, means for exciting said transmitter sub-array during Doppler operation to sequentially generate ultrasound pulses that are transmitted along a chosen beam direction intersecting a sample volume through which the true velocity vector is being measured, the received echo signals being coherently demodulated and time delayed as in B-scan mode except that in alternate ultrasound pulse repetition intervals the phase of the phase quadrature references in a left or right group of receiving channels is reversed by $\pi$, and means for generating left and right focused in-phase and quadrature signals, computation means for deriving in-phase and quadrature Doppler signals for the beam direction and transverse direction realized by combining four signals representing the differences and sums of the four left and right focuses signals, a range gate for extracting analog samples from said Doppler signals after every pulse transmission period at a time corresponding to reception of echoes backscattered from the sample volume, a Doppler processor for deriving from sets of said analog samples two components of velocity parallel to and transverse to the beam direction, and means for vectorially summing the two components to realize the time flow velocity vector.

11. The duplex system of claim 10 wherein said computation means for Doppler signals is comprised of summing circuits for producing two difference and two sum signals representing the differences and sums of the left and right focused in-phase and quadrature signals, an interpolation filter through which pass said difference and sum signals, and multipliers and summers for producing said Doppler signals from different combinations of said four difference and sum signals.

12. The duplex system of claim 11 wherein said Doppler processor is a dual channel real time digital Fast Fourier Transform processor.

13. The duplex system of claim 12 further including Doppler display means comprised of at least a strip chart recorder for presenting true bidirectional velocity as a function of time.

14. A method of measuring the true flow velocity of blood and similar liquids by use of an ultrasound system having a linear array of piezoelectric elements which are divisible into a central transmitter sub-array and left and right receiver sub-arrays comprising the steps of:

exciting said transmitter sub-array to sequentially generate pulses of ultrasound that propagate along a chosen beam direction and insonify a sample volume in the object being examined through which the true velocity vector is being determined, locating the positions of said receiver sub-arrays such that center wave vectors through the sample volume subtend approximately equal angles with respect to a transmitter wave vector through the sample volume, and alternately after every pulse transmission detecting received echoes and generating electrical echo signals, processing the echo signals in a left group and right group of receiving channels, each having in-phase and quadrature channels in which the echo signals are coherently demodulated using phase quadrature emission frequency reference signals and are timed delayed and summed to generate left and right focused in-phase and quadrature signals, computing in-phase and quadrature Doppler signals for the beam direction and for the transverse direction from combinations of the four left and right focused signals, gating said Doppler signals for a short interval after every pulse transmission to extract two pairs of analog samples representing echoes backscattered from the sample volume, analyzing sets of said pairs of analog samples with a Doppler processor to realize two components of velocity parallel to and transverse to the beam direction, and vectorially summing the two components to realize the true flow velocity vector.

15. The method of claim 14 wherein the step of processing echo signals in left and right groups of receiving channels which are demodulated using phase quadrature reference signals comprises reversing the phase of the reference signals in one group of channels by $\pi$ in alternate ultrasound pulse repetition intervals.

16. The method of claim 15 wherein the step of computing Doppler signals comprises producing two difference signals representing the differences of the left and right focused in-phase signals and left and right focused quadrature signals, two sum signals representing the sums of the left and right focused in-phase signals and left and right focused quadrature signals, and producing the four Doppler signals by different combinations of said difference and sum signals.

17. A method of measuring the transverse component of the flow velocity of blood and similar liquids at right angles to an acoustic beam direction by use of an ultrasound system having a linear array of piezoelectric elements which are divisible into a central transmitter sub-array and left and right receiver sub-arrays, the transverse component to be vectorially summed with a component parallel to the beam direction to realize the true velocity vector, comprising the steps of:

exciting said transmitter sub-array to sequentially generate pulses of ultrasound that propagate along a chosen beam direction and insonify a sample volume in the object being examined through which the true velocity vector is being determined, locating the positions of said receiver sub-arrays such that center wave vectors through the sample volume subtend approximately equal angles with respect to a transmitter wave vector through the sample volume, and alternately after every pulse transmission detecting received echoes and generating electrical echo signals, processing the echo signals in a left group and right group of receiving channels, each having in-phase and quadrature channels in which the echo signals are coherently demodulated using phase quadrature emission frequency reference signals and are time delayed and summed to generate left and right focused in-phase and quadrature signals, computing in-phase and quadrature Doppler signals for the transverse direction from combinations of the four left and right focused signals, gating said Doppler signals for a short interval after every pulse transmission to extract a pair of analog samples representing echoes backscattered from the sample volume, and analyzing sets of said pairs of analog samples with a Doppler processor to realize the component of velocity transverse to the beam direction.

* * * * *